United States Patent [19]

Wahlefeld et al.

[11] 4,162,979
[45] Jul. 31, 1979

[54] DEVICE FOR THE CHEMICAL AND/OR PHYSICAL TREATMENT OF LIQUIDS

[75] Inventors: August W. Wahlefeld; Siegfried Looser, both of Weilheim; Klaus A. Sturmann, Oberalting-Seefeld, all of Fed. Rep. of Germany

[73] Assignee: Boehringer Mannheim GmbH, Mannheim-Waldhof, Fed. Rep. of Germany

[21] Appl. No.: 843,299

[22] Filed: Oct. 18, 1977

[30] Foreign Application Priority Data

Nov. 22, 1976 [DE] Fed. Rep. of Germany ....... 7636679

[51] Int. Cl.² .............................................. B01D 27/02
[52] U.S. Cl. .................... 210/282; 210/477; 210/479; 210/DIG. 24; 422/101
[58] Field of Search ............... 210/DIG. 23, DIG. 24, 210/514–518, 455, 477–479, 424, 282; 23/292; 422/99, 101

[56] References Cited

U.S. PATENT DOCUMENTS

| 152,981 | 7/1874 | Donkin | 210/479 |
|---|---|---|---|
| 3,625,652 | 12/1971 | Fujimoto et al. | 23/292 X |
| 3,647,070 | 3/1972 | Adler | 210/516 X |
| 3,661,265 | 5/1972 | Greenspan | 210/DIG. 24 |
| 3,701,434 | 10/1972 | Moore | 210/DIG. 24 |
| 3,807,955 | 4/1974 | Note, Jr. et al. | 210/DIG. 24 X |
| 3,969,250 | 7/1976 | Farr | 210/DIG. 23 |
| 4,035,150 | 7/1977 | Jaffe | 210/DIG. 24 |

FOREIGN PATENT DOCUMENTS

2415618 10/1975 Fed. Rep. of Germany ... 210/DIG. 23

OTHER PUBLICATIONS

Aloe Scientific, pp. 435–437, Cat. #103, 1952.
Fisher Scientific, pp. 471–472, Cat. #63, 1962.

*Primary Examiner*—Ferris H. Lander
*Attorney, Agent, or Firm*—Sprung, Felfe, Horn, Lynch & Kramer

[57] ABSTRACT

A device for the chemical and/or physical treatment of liquids which comprises a flowthrough vessel having an inlet and an outlet and is receptive of a treatment agent therebetween. The vessel comprises a substantially cylindrical tube having one end at the outlet and a conically widening tube section connected to the other end of the cylindrical tube. A permeable carrier is mounted in the cylindrical tube at the outlet end to support the treatment agent placed in the cylindrical tube.

11 Claims, 1 Drawing Figure

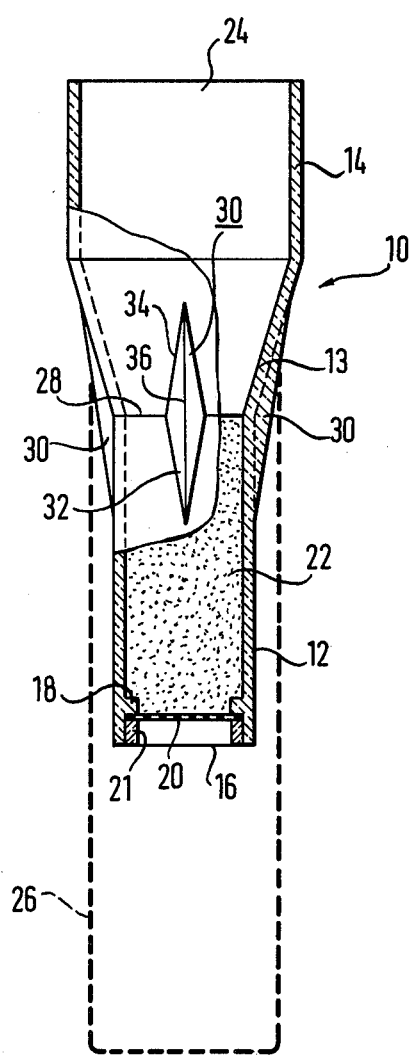

DEVICE FOR THE CHEMICAL AND/OR PHYSICAL TREATMENT OF LIQUIDS

The present invention relates to a device for the chemical and/or physical treatment of liquids, comprising a flow-through vessel with an inlet, an outlet and a reception space for a treatment agent between the inlet and the outlet.

It is an object of the present invention to provide a device which is so simple in its construction that it can be used as a cheap adjunct for physical and/or chemical treatment agents, for example reagent media, for the treatment and/or investigation of body fluids and, in extreme cases, can be regarded as a disposable article which, after having been used once, can be discarded.

Thus, according to the present invention, there is provided a device for the chemical and/or physical treatment of liquids, comprising a flowthrough vessel with an inlet, an outlet and a reception space for a treatment agent between the inlet and the outlet, the flowthrough vessel being constructed with a substantially cylindrical tube on the outlet side and a conically widening tube section connected to the upper end of said cylindrical tube and, close to the outlet end of said cylindrical tube, there is provided a permeable carrier for a treatment agent to be placed in the cylindrical tube.

On or near the lower end of the cylindrical tube, there is preferably provided a supporting shoulder for the permeable carrier. This permeable carrier is advantageously in the form of a sieve and can be, for example, a glass frit or a synthetic resin fabric, such as a polyamide fabric.

On the inlet end of the widened conical section, there is preferably attached a cylindrical tube.

According to a preferred embodiment of the device, in the transitional region between the cylindrical tube and the conical tube section, on the outer side thereof, there are arranged bearing members adapted to bear on the upper edge of a collection vessel, such as a test tube, for receiving the cylindrical tube.

These bearing members are preferably constructed in the form of roof-shaped ribs, each of which forms, with the cylindrical tube and the conical section, an acute-angled triangular member, the gable lines of these ribs bridging the hollow throat in the transition region between the cylindrical tube and the conical tube section.

The diameter of the cylindrical tube is preferably so dimensioned that it can be introduced into the open end of a test tube.

The flowthrough vessel is preferably made of a transparent material, such as a synthetic resin.

The permeable carrier can be introduced from the outlet end of the cylindrical tube so as to lie against the supporting shoulder and is held securely against this shoulder by a holding ring, which can be in the form of a spring ring, which is also introduced from the outlet end of the cylindrical tube and is tensioned against the inner wall of the cylindrical tube.

For a better understanding of the present invention, reference will be made to the accompanying drawing, which is a sectional view of one embodiment thereof.

Referring now to the accompanying drawing, a flowthrough vessel 10 comprises a lower part constructed in the form of a cylindrical tube 12, a middle part in the form of an upwardly conically widening tube section 13 and an upper part in the form of a cylindrical tube section 14.

Close to outlet 16 of the cylindrical tube 12, there is provided a supporting shoulder 18 for a carrier sieve 20. On this carrier sieve 20, there rests a physical and/or chemical treatment agent 22 which substantially fills only the cylindrical tube 12. The treatment agent can, for example, be present in granular form. The liquid to be treated is introduced through upper open end 24 of the cylindrical tube section 14 and flows through the treatment agent 22 and the carrier sieve 20 to the outlet 16 into a collection vessel 26 (indicated by broken lines), for example a test tube. The conically widened tube section 13 and the cylindrical tube section 14 accommodate a supply of the liquid to be treated.

In the region of hollow throat 28 between the cylindrical tube 12 and the conical tube section 13 are provided bearing members 30 which are adapted to bear on the upper edge of the test tube 26 in such a manner that, between the flowthrough vessel 10 and the upper edge of the reagent glass 26, a gap remains free to permit the escape of air. The bearing members 30 are constructed as roof-shaped ribs, each of which forms, with the cylindrical tube 12 and the conical tube section 13, an acute-angled triangular member (32 or 34), whereas gable line 36 bridges the hollow throat 28.

The carrier sieve 20 is introduced from below into the cylindrical tube 12 and lies against the shoulder 18 where it is held in position by a spring ring 21 made of synthetic resin.

It will be understood that the specification and examples are illustrative but not limitative of the present invention and that other embodiments within the spirit and scope of the invention will suggest themselves to those skilled in the art.

What is claimed is:

1. A device for the treatment of liquids, comprising a flowthrough vessel having an inlet and an outlet and containing therein a treatment agent between the inlet and the outlet, the flowthrough vessel comprising a substantially cylindrical tube having one end at the outlet and a conically widening tube section connected to the other end of said cylindrical tube and, integral therewith, a permeable carrier configured to be insertable into the cylindrical tube through the outlet end thereof for supporting thereupon the treatment agent within the cylindrical tube and means for maintaining the permeable carrier in position within the cylindrical tube, said means comprising a supporting shoulder extending radially inwardly from the inner wall of the cylindrical tube at the outlet end, wherein the permeable carrier, after insertion, rests against the shoulder and a holding ring configured to be insertable through the outlet end of the cylindrical tube abutting the permeable carrier and to be tensioned directly against the inner wall of the cylindrical tube to securely hold the permeable carrier between same and the supporting shoulder.

2. A device as claimed in claim 1 wherein the permeable carrier is a sieve.

3. A device as claimed in claim 2 wherein the carrier sieve is a glass frit.

4. A device as claimed in claim 2 wherein the carrier sieve consists of a synthetic resin fabric.

5. A device as claimed in claim 4 wherein the synthetic resin fabric is a polyamide fabric.

6. A device as claimed in claim 1 further comprising a second cylindrical tube connected at one end to the other end of the widened conical tube section.

7. A device as claimed in claim 1 wherein the flow-through vessel is composed of a transparent material.

8. A device as claimed in claim 1 wherein the transparent material is a synthetic resin.

9. A device as claimed in claim 1 wherein the holding ring comprises a spring ring.

10. A device for the treatment of liquids, comprising a flowthrough vessel having an inlet and an outlet and containing therein a treatment agent between the inlet and the outlet, the flowthrough vessel comprising a substantially cylindrical tube having one end at the outlet and a conically widening tube section connected to the other end of said cylindrical tube and integral therewith, bearing members disposed in the transitional region between the cylindrical tube and the conical tube section, on the outer side thereof for bearing on the upper edge of a collection vessel receptive of the cylindrical tube said bearing members comprising roof-shaped outwardly extending ribs, each of which forms, with the cylindrical tube and the conical section, an acute-angled triangular member, and having gable lines bridging the hollow throat in the transition region between the cylindrical tube and the conical tube section.

11. A device as claimed in claim 10 wherein the diameter of the cylindrical tube is configured to be introduced into the open end of a test tube.

* * * * *